United States Patent [19]

Rose

[11] 4,046,151
[45] Sept. 6, 1977

[54] BODY IMPLANTABLE LEAD WITH STIFFENING STYLET

[75] Inventor: Maria M. Rose, Wayzata, Minn.

[73] Assignee: Medtronic, Inc., Minneapolis, Minn.

[21] Appl. No.: 682,506

[22] Filed: Apr. 30, 1976

[51] Int. Cl.² .............................................. A61N 1/04
[52] U.S. Cl. .............................. 128/404; 128/349 R; 128/418; 128/419 P
[58] Field of Search ................... 128/404, 418, 419 P, 128/349 R, 351, 2 M

[56] References Cited

U.S. PATENT DOCUMENTS

| | | | |
|---|---|---|---|
| 3,348,548 | 10/1967 | Chardack | 128/419 P |
| 3,460,541 | 8/1969 | Doherty | 128/351 |
| 3,750,650 | 8/1973 | Ruttgers | 128/418 |
| 3,974,834 | 8/1976 | Kane | 128/419 P |

FOREIGN PATENT DOCUMENTS 1,277,107   6/1972   United Kingdom ............. 128/419 P Primary Examiner—William E. Kamm
Attorney, Agent, or Firm—Joseph F. Breimayer; Harry W. Barron

[57] ABSTRACT

A body implantable lead and stiffening stylet for imparting rigidity and transmitting torque to the distal end of the lead for enabling the attachment of the lead to an internal body organ. The intravascular lead carries a pin or pins at its proximal end adapted to be connected to a pulse generator and an electrode or electrodes at its distal end adapted to be securely lodged in or permanently attached to a body organ through endothelial tissue. The stiffening stylet is provided for insertion into a lumen in the lead extending from the pin along the length of the conductor to the electrode. The portion of the stylet wire to be inserted in the lumen is of a length somewhat exceeding the corresponding length of the lumen. At the proximal end of the stylet a knob is provided to engage the pin and thereby stretch the lead to effect an increase in its stiffness and torque transmitting ability.

15 Claims, 5 Drawing Figures

U.S. Patent  Sept. 6, 1977  4,046,151
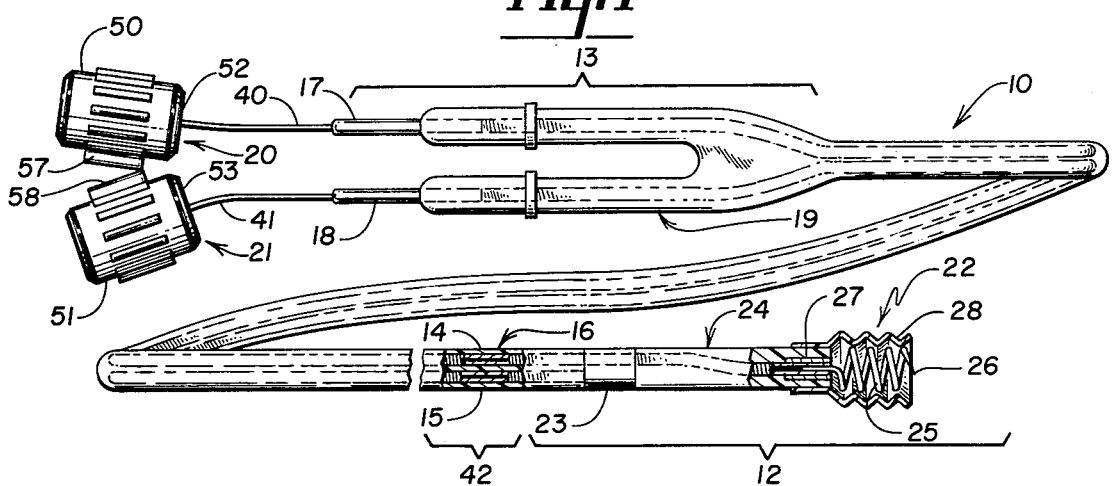
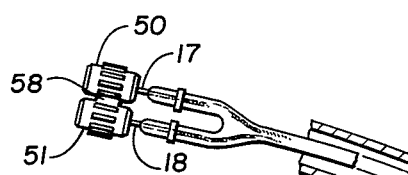
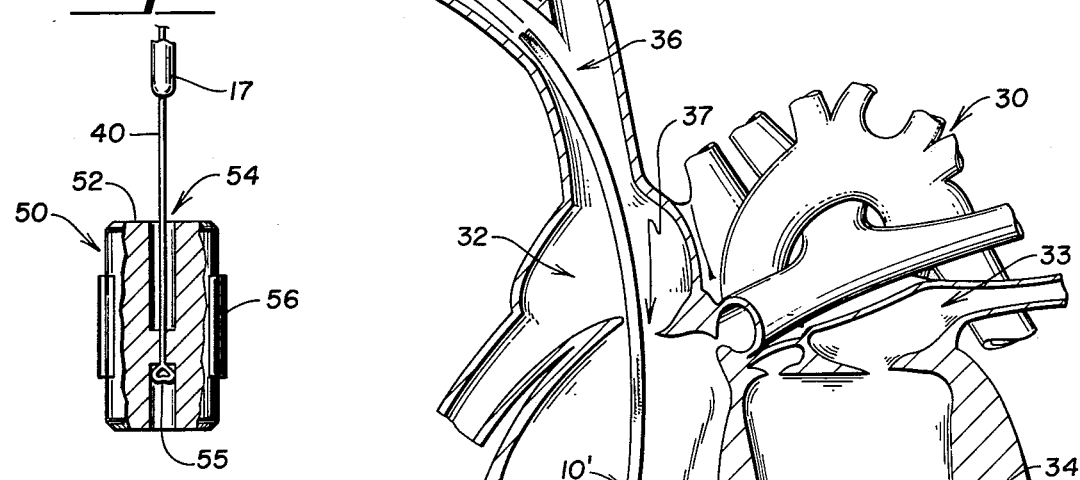
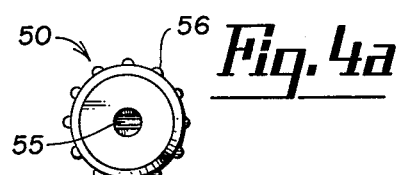
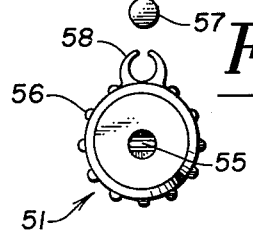

BODY IMPLANTABLE LEAD WITH STIFFENING STYLET

BACKGROUND OF THE INVENTION

This invention relates to a body implantable lead bearing an electrode for connecting a living body organ to an electrical device, and more particularly to the combination of such a lead with an improved stiffening stylet. Notwithstanding its various uses, this invention will be described as an endocardial pacing and sensing lead for connecting a pacemaker pulse generator to cardiac tissue.

Endocardial pacing and sensing leads of the types shown in U.S. Pat. No. 3,348,548, for example, comprise one or more lengths of hollow, coiled wire conductor encased within a suitable insulating material, such as silicone rubber, that is substantially inert to body fluids and tissues, a hollow connector pin attached to the proximal end of each conductor, and an electrically conductive electrode at the distal end of the conductor adapted to be placed in contact with the endocardium of a patient. A lumen extends through each pin and the corresponding length of coiled wire conductor to the electrode at the distal end thereof and receives a stiffening stylet of cylindrical stainless steel wire for imparting stiffness to the lead to facilitate its advancement through the venous system of the patient and into the apex of the right ventricle. With the stylet removed from the lead, the lead is very flexible and difficult to so advance. Further details of the construction and utility of such an endocardial pacing lead may be obtained by reference to the aforementioned U.S. Pat. No. 3,348,548.

The conventional endocardial pacing lead employs a relatively blunt tip electrode at its distal end that is adapted to be lodged in the trabeculae at the apex of the right ventricle. An improved endocardial pacing lead employing a rigid, electrically conductive helix with a sharp tip at the distal end of the lead adapted to be screwed into the endocardium is disclosed in copending U.S. Pat. No. 3,974,834 issued Aug. 17, 1976 entitled BODY IMPLANTABLE LEAD and assigned to Medtronic, Inc. The improved lead can be lodged in and permanently secured to or removed from body tissue without the use of complex electrode advancement mechanisms or bulky sleeves or catheter introducers to protect the patient's veins and tricuspid valve from snagging on the sharp tip of the helix. Placement of this improved body implantable lead is effected through the employment of a shroud of resilient non-conductive material extending from the silicon rubber casing of the lead through the length of the helix that is adapted to retract upon contact with tissue as the helical electrode is screwed therein. One or more conventional stylets of stainless steel wire are employed to stiffen the improved body implantable lead during the introduction and placement thereof.

The body implantable lead of the present invention incorporates an improved stylet or stylets that increase their effectiveness in the placement of either the conventional, endocardial leads of the type disclosed in the aforementioned U.S. Pat. No. 3,348,548 or the improved helical electrode lead. One of the features of the present invention is the provision of a stylet adapted to stretch and lengthen the helical wire conductor beyond its relaxed length to increase the rigidity of the lead and the ability of the lead to transmit torque from its proximal end to its distal end.

SUMMARY OF THE INVENTION

The above features and advantages of the present invention, as well as other, are accomplished by providing a body implantable, intravascular lead of the type having a lumen for receiving a stiffening stylet extending through the connector pin of the lead at its proximal end, through the length of the lead and to the electrode at the distal end thereof with an improved stiffening stylet having means for selectively stretching the lead beyond its normal length to increase the torsional rigidity of the lead. The improved stiffening stylet further comprises a length of stylet wire and a knob at the distal end thereof having a bore adapted to receive and frictionally engage the connector pin of the lead through a selected range of advancement of the length of stylet wire into the lumen of the lead, thereby stressing the lead and increasing its torsional and axial rigidity. In addition, the mating of the bore and pin enables the rotation of the stylet and the entire lead by rotation of the knob.

In a bipolar, body implantable lead of the type having a pair of connector pins, conductors and electrodes of the type hereinbefore described in a unitary structure, a corresponding pair of improved stiffening stylets may be provided, wherein the knobs of the stiffening stylets carry attaching members for connecting the knobs together. When connected together, the pair of stylets acts as a unitary member to increase the stiffness and torsional rigidity of the lead and facilitates the direct transmission of torque applied by rotation of the attached knobs directly to the distal end of the lead.

Preferably, the electrode carried by the lead comprises a rigid helix or corkscrew of suitable conductive electrode material, the helix being adapted to be screwed into endothelial tissue through the rotation of the lead and the stiffening stylet or stylets extending therein.

Furthermore, the conductor(s) of the lead is preferably of coiled wire construction, the coiled wire extending within a lumen(s) in a resilient casing material, the coiled wire conductor being adapted to stretch within the resilient casing on the full advancement of the stylet wire.

Other features, advantages and objects of the present invention will hereinafter become more fully apparent from the following description of the drawings, which illustrate a preferred embodiment of the invention.

BRIEF DESCRIPTION OF THE DRAWINGS

FIG. 1 shows a view of a preferred embodiment of the body implantable, intravascular lead of the present invention including in part and in side elevation partly on longitudinal section of the distal portion of the lead and including a depiction of the improved stiffening stylets partly inserted in the lumens of the lead;

FIG. 2 shows the lead of FIG. 1 being lodged in and permanently secured to the tissue forming the apex of the right ventricle of the heart;

FIG. 3 is a detail drawing, partly in longitudinal section, of the knob and a portion of the wire of the improved stiffening stylet; and FIGS. 4a and 4b depict end views of a pair of knobs of FIG. 3 adapted to be attached together.

DESCRIPTION OF THE PREFERRED EMBODIMENT

Referring now to the preferred embodiment of the invention depicted in FIG. 1, there is shown the improved intravascular endocardial lead fully described in the aforementioned U.S. patent application Ser. No. 570,917 comprising an elongated lead portion 10, a distal electrode end portion 12 and a proximal terminal end portion 13. The lead, in bipolar configuration, comprises a pair of closely wound, coiled conductors 14, 15 each in the form of a spring spirally wound about and along the axis of the conductor. The spring coil conductors 14, 15 extend through the length of the lead 10 in separate lumens of a jacket or sleeve 16 of electrically insulating material, the coils 14, 15 having the capability of stretching and flexing independently of one another and the sleeve 16.

Each spiral conductor 14, 15 is formed of electrically conductive material offering low electrical resistance and also resistent to corrosion by body fluids. A platinum-iridium alloy is an example of a suitable material. Sleeve 16 is formed of an electrically insulating material, and preferably a silicone rubber such as clean room grade Silastic available from Dow Corning Corporation. This material is additionally suitable because it is inert and well tolerated by body tissue.

At the proximal end 13 of the lead 10, the conductors 14 and 15 are received in and crimped to tubular terminal pins 17 and 18, respectively. A bifurcated boot 19 of the same material as jacket 16 is molded about the terminal pins 17, 18 and the terminal ends of coils 14 and 15 and jacket 16, with the pins 17 and 18 projecting therebeyond. These pins are adapted for insertion in receptacles provided on the pulse generator, which can comprise any suitable implantable pulse generator such as that shown, for example, in U.S. Pat. No. 3,057,356.

At the distal end of the lead 10, a pair of electrodes 22 and 23 are welded or otherwise electrically connected to the ends of the conductors 14 and 15, respectively. The electrode 23 preferably takes the form of a ring of corrosion resistant, electrically conductive material, e.g., platinum or a platinum alloy, a metal oxide or a carbon compound. The ring electrode 23 encircles both coiled conductors 14 and 15. Electrode 22 is similarly electrically connected to the distal end of coiled conductor 14, and the length of coiled conductor 14 extending between electrodes 22 and 23 is insulated by a jacket 24 of the same material as the sleeve 16 molded thereto. In this way, the entire lead is electrically insulated when it is connected to the pulse generator from the body except at the electrodes 22 and 23.

The lead 10 of FIGS. 1 and 2 as described hereinbefore corresponds to that disclosed in U.S. Pat. No. 3,348,548. The lead 10 thus far described has been shown to be capable of withstanding constant, rapidly repeated flexing over a period of time which can be measured in years. The conductor coils are wound relatively tightly, although there can be a slight space between adjacent turns. This closely coiled construction provides a maximum number of conductor turns per unit length, thereby providing optimum strain distribution. The spirally coiled spring construction of the conductors also permits a substantial degree of elongation, within the elastic limits of the material, as well as distribution along the conductor of flexing stresses which otherwise might be concentrated at a particular point. Both the conductors 14 and 15 and the insulating bodies 16, 19 and 24 are elastic, and this, together with the coiled construction of the conductors, assures maximum distribution of flexing strains.

In addition, the lead of FIG. 1 comprises the electrode 22 which further comprises tissue piercing and retaining means and an integral introducer sleeve means for protecting intravascular body vessels from damage by the tissue piercing means during insertion and guidance of the lead that on its own accord retracts from the tissue piercing and retaining means as the same are advanced into and/or through endothelial tissue. More specifically, the electrically conductive electrode 22 is formed in the shape of a circular corkscrew of helix 25 having about five turns extending about ¼ inch in length and having a nominal outside diameter approximating that of the insulated body of the lead 10, e.g., about 3.2 mm. The helix 25 may be insulated by a thin nonconductive material except for its tip or one or more turns or a portion thereof, so that stimulation current density may be increased in proportion to the conductive electrode area. The helix 25 is welded or otherwise electrically connected to a terminal junction 27 of the conductor 14. Preferably, the helix 25 has a sharpened tip 26 for piercing endocardial tissue and a sufficient number of turns so that as the lead 10 and electrode 22 is rotated by rotation of the proximal terminal end portion 13, the helix 25 may advance through the endocardial tissue into myocardial tissue and be retained therein and inhibited from dislodgement therefrom by the turns of the helix 25.

An introducer sleeve or shroud 28 is fitted over the turns and tip 26 of the helix 25 and sealed to the jacket 24 about the junction 27. The introducer sleeve 28 is made entirely of a silicon rubber compound or other suitable material in a configuration of a thin-walled, accordian-like pleated tube having a number of pleats at least equal to and accommodating the turns of the corkscrew electrode 25. When relaxed, as shown in FIG. 1, the pleats are extended and form 90° angles with respect to one another. The sleeve 28 in its relaxed state is about 0.3 inch in length, has an outside maximum pleat diameter of about 0.16 inch and a wall thickness of about 0.01 inch.

The introducer sleeve 28 is designed to afford protection to the body vessel or vein through which the lead is introduced and to the endothelial tissue of a body organ until the desired implantation position is reached. In the cardiac pacemaker application, once the lead is in the ventricle and is ready to be secured in the desired position of the endocardium, the accordian-like pleats of the sleeve 28 will collapse and fold back over the turns of the helix 25 as it is screwed into the endocardium.

Referring now to FIG. 2, there is shown an illustration of the completed introduction and permanent securement of the electrode 22 in the tissue forming the apex of the right ventricle of a heart.

In FIG. 2, the heart 30 in cross-section comprises the four chambers, namely, the right ventricle 31, the right atrium 32, the left atrium 33 and the left ventricle 34. In the placement of an endocardial lead, it is preferable to use a venous approach on the low pressure side of the heart, that is, through a vein, e.g., the right or left external jugular veins or the right or left cephalic veins 35, the superior vena cava 36, the right atrium 32, the tricuspid valve 37 and the right ventricle 31. During introduction of the lead 10, it must travel a convoluted course through the veins and must pass through the valve 37 without causing any damage to the tissue. It is also desirable that the lead 10 have a small cross-section so that it will easily pass through the veins without causing excessive stretching of the veins.

The lead 10' is illustrated screwed into the endocardium at the apex of the right ventricle 31. The helix 25' is fully screwed in by rotation of the entire lead by manipulation of the proximal end 13 of the lead 10'. As it is pressed against the endocardium during the rotation of the lead 10', the sleeve 28' progressively collapses back in its pleats, and the turns of the helix 25' slip past the open end of the sleeve 28' and turn into the cardiac tissue.

In clinically testing the operation of the lead 10 of the present invention, it has been found that the corkscrew or helix 25 can be easily and repeatedly introduced through the vein, through the valve and screwed into the endocardium, unscrewed and withdrawn from the body through the same path without causing any significant damage to the tissue that the lead contacts. As the lead is unscrewed, the pleats of the sleeve 28' expand and the sleeve slips back over the turns of helix 25.

Turning now to the improvements of the present invention, reference is made to the stylets 20, 21 and the proximal end 13 of the lead 10 of FIGS. 1 and 2. The stylets 20, 21 comprise stylet wires 40, 41 of cylindrical, stainless steel wire having predetermined lengths and knobs 50, 51 attached to the proximal ends of the wires 40, 41 in a manner to be described in reference to FIG. 3. The stylet wires 40, 41 extend through central lumens in pins 17, 18 and conductors 14, 15 to terminal points within crimping member 27 and ring electrode 23. The stylet wires 40, 41 are depicted as passing through the exposed lumens of conductors 14, 15 at section 42 in FIG. 1. The lumen of conductor 14 is depicted as extending to the folded end of helix 25 within crimping member 27 at distal end 12.

The stylets 20, 21 are depicted in FIG. 1 as partially withdrawn from the lumens of the lead 10 and are depicted in FIG. 2 as fully extended into the lumens. The lengths of stylet wires 40, 41 extending from the faces 52, 53 of knobs 50, 51 are selected to correspond to the respective lengths of the lumens in conductors 14, 15. Therefore, the stylet wire 40 will be longer than the wire 41 to account for the distance between the terminal points of the respective lumens at electrodes 22 and 23.

In FIG. 2, the stylets 20, 21 are depicted as fully extended into the lumens. The knobs 50, 51 are depicted as advanced part way onto the pins 17, 18 and attached together. When the knobs so engage the pins 17, 18, an additional length of stylet wire 40, 41 on the order of 0.5 cm. is inserted into the lumen, thereby stretching the lead 10. The stretching action places tension on the coiled wire conductors 14, 15 and 16 relatively rigid and increases its ability to transmit torque applied to its proximal end to its distal end.

Turning now to FIG. 3, there is shown partly in section an elevation of the knob 50 (for example) and a section of stylet wire 40 attached thereto and extending into pin 17. FIG. 3 depicts the axial bore 54 through which wire 40 axially extends and into which pin 17 is forced (as shown in FIG. 2). Knob 50 is manufactured of a nonconductive plastic, for example, and retains the proximal end 55 of wire 40 extending through the bore 54 in the manner depicted.

Bore 54 is gradually tapered, and the reduction in the diameter thereof provides a frictional fit with the pin 17, thereby stretching the lead 10. The degree to which the lead 10 may be stretched is dependent upon the surgeon's preference, since one or both of the knobs 50, 51 may be pressed on the corresponding pin 17, 18, and the pins 17, 18 may be forced all or only part of the way into bore 54.

The circumference of the knobs 50, 51 is provided with a number of splines 56 for enabling the surgeon to securely grip the knobs 50, 51 in the implantation operation. With reference to FIGS. 4a and 4b, the splines 56 are shown as equidistantly arranged around the circumference of the knobs 50, 51.

FIGS. 4a and 4b are end views of the knobs 50, 51, respectively, and depict the male and female attaching members 57, 58, respectively. The members 57, 58 are about the same length as and replace one of the splines 56 on each knob 50, 51. The male member 57 is adapted to snap into the female member 58 and thereby make the knobs 50, 51 act as a single element. As shown in FIG. 2, when the knobs 50, 51 are attached together and are forced onto the pins 17, 18, the entire proximal end 13 of the lead may be rotated through rotation of the attached knobs 50, 51. It should be noted that the length of members 57, 58 allow the surgeon to force one of the knobs 50, 51 into the respective pins 17, 18 a further distance than the other. The members 57, 58 will still engage one another.

With respect to the operative procedure for attaching the lead 10 to the heart 30 of FIG. 2 hereinbefore described, the attached knobs 50, 51 impart to the lead 10 a tension and degree of stiffness and torque transmissibility that enables the surgeon to readily screw the electrode 22 into the endocardium. The lead 10 is contrained from twisting and coiling upon itself when the proximal end is rotated. The desired rotation is directly transmitted from the proximal end to the distal electrode 22, enabling it to be readily screwed into or out of the endocardium.

Although a bipolar lead design has been illustrated in the description of the preferred embodiment, it will be understood that unipolar leads (that is, a lead carrying but one electrode and conductor) may as readily employ the novel electrode design of the present invention. Also, it should be understood that other electrode designs or positions along the lead could be substituted for that of the electrode 22. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventor of many possible modes of practicing the invention and that numerous modifications may be made therein without departing from the spirit and scope of the invention as set forth in the appended claims.

What is claimed is:

1. A body implantable lead of material substantially inert to body fluids and tissue comprising a length of electrically insulated, flexible conductor, a connector element at the proximal end of the conductor, an electrode adapted to contact the tissue of a living animal body at the distal end of the conductor, a lumen extending the length of insulated conductor, and a stiffening stylet, said stylet further comprising:

stylet wire means for insertion into said lumen for stiffening said electrical conductor, said stylet wire means having a length exceeding the length of said lumen; and means coupled to said stylet wire means at one end thereof for engaging said connector element upon insertion of said length of said stylet wire means into said lumen and for maintaining the engagement and lengthening said conductor for increasing the transmission of torque from said proximal end to said distal end of said lead.

2. The body implantable lead of claim 1 wherein said engaging means further comprises knob means having bore means for receiving and frictionally engaging said connector element.

3. The body implantable lead of claim 2 wherein said stylet wire means extends axially into said bore means, and said connector element comprises a pin for receiving said stylet wire means.

4. The body implantable lead of claim 3 wherein said bore means has a predetermined length and a tapered diameter, and said pin has an outside diameter exceeding at least a portion of the tapered diameter of said bore means.

5. A body implantable lead of material substantially inert to body fluids and tissue comprising first and second lengths of electrically insulated, flexible conductor, first and second respective connector elements at the proximal ends of said conductors, first and second respective electrodes adapted to contact the tissue of a living animal body at the distal ends of the conductors, first and second respective lumens extending the lengths of insulated conductors and a first stiffening stylet, said stylet further comprising:
   stylet wire means for insertion into said first respective lumen for stiffening said electrical conductor, said stylet wire means having a length exceeding the length of said first lumen; and
   means coupled to said stylet wire means at one end thereof for engaging said connector element upon insertion of said length of said stylet wire means into said lumen and for maintaining the engagement and lengthening said conductor for increasing the transmission of torque from said proximal end to said distal end of said lead.

6. The body implantable lead of claim 5 wherein said engaging means further comprises knob means having bore means for receiving and frictionally engaging said connector element.

7. The body implantable lead of claim 6 wherein said stylet wire means extends axially into said bore means, and 8. The body implantable lead of claim 7 wherein said bore means has a predetermined length and a tapered diameter, and said pin has an outside diameter exceeding at least a portion of the tapered diameter of said bore means.

9. The body implantable lead of claim 5 further comprising: a second stiffening stylet comprising further stylet wire means for insertion into said second respective lumen for stiffening said electrical conductor, and further engaging means coupled to the proximal end of said further stylet wire means and wherein said further engaging means further comprises attaching means for attaching both said engaging means together and for coupling said first and second connector elements and both said stylet wire means together.

10. The body implantable lead of claim 9 wherein said engaging means of said first and second stylets comprise first and second knob means, respectively, and said attaching means further comprises a male coupling member carried by said first knob means and a female coupling member carried by said second knob means.

11. The body implantable lead of claim 9 wherein at least one of said electrodes comprises a helical coil with a sharp tip adapted to be screwed into body tissue.

12. A body implantable lead of material substantially inert to body fluids and tissue having a length of electrically insulated, flexible conductor, an electrode adapted to contact the tissue of a living animal body at the distal end of the conductor, and a lumen extending the length of insulated conductor, said lead further comprising:
   stylet wire means for insertion into said lumen for stiffening said electrical conductor, said stylet wire means having a length exceeding the length of said lumen; and
   means coupled to said stylet wire means for engaging with said lead and holding at least a portion of the excess length of said stylet wire means in said lumen for increasing the tension on said lead.

13. A body implantable lead of material substantially inert to body fluids and tissue having first and second lengths of electrically insulated, flexible conductor, first and second respective connector elements at the proximal ends of said conductors, first and second respective electrodes adapted to contact the tissue of a living animal body at the distal ends of the conductors, first and second respective lumens extending the lengths of insulated conductors and first and second respective stiffening stylets, each stylet further comprising:
   stylet wire means for insertion into a respective lumen for stiffening said electrical conductor; and
   attaching means coupled to said stylet wire means for coupling said first and second stylets together at the proximal end of said lead.

14. The body implantable lead of claim 13 wherein said first and second stylets comprise first and second knob means, respectively, and said attaching means further comprises a male coupling member carried by said first knob means and a female coupling member carried by said second knob means.

15. The body implantable lead of claim 13 wherein at least one of said electrodes comprises a helical coil with a sharp tip adapted to be screwed into body tissue.

* * * * *

UNITED STATES PATENT OFFICE
CERTIFICATE OF CORRECTION

Patent No. 4,046,151           Dated September 6, 1977

Inventor(s) Maria M. Rose

It is certified that error appears in the above-identified patent and that said Letters Patent are hereby corrected as shown below:

Col. 3, Lines 7 and 8, "patent application Ser. No. 570,917" should be --Patent No. 3,974,834--;

Line 21, "resistent" should be --resistant--.

Col. 4, Line 13, "of" (second occurrence) should be --or--;

Line 36, "accordian" should be --accordion--;

Line 50, "accordian" should be --accordion--.

Col. 6, Line 33, "trained" should be --strained--.

Col. 7, Line 48, after "and" insert --said connector element comprises a pin for receiving said stylet wire means and for extending into said bore means.--.

Signed and Sealed this

Twenty-seventh Day of December 1977

[SEAL]

Attest:

RUTH C. MASON  
Attesting Officer

LUTRELLE F. PARKER  
Acting Commissioner of Patents and Trademarks